United States Patent
Shinoda

(10) Patent No.: US 10,149,632 B2
(45) Date of Patent: Dec. 11, 2018

(54) MAGNETIC RESONANCE IMAGING APPARATUS AND IMAGING PLANNING METHOD

(71) Applicant: TOSHIBA MEDICAL SYSTEMS CORPORATION, Otawara-shi (JP)

(72) Inventor: Kensuke Shinoda, Tochigi (JP)

(73) Assignee: TOSHIBA MEDICAL SYSTEMS CORPORATION, Otawara-Shi, Tochigi-Ken (JP)

(*) Notice: Subject to any disclaimer, the term of this patent is extended or adjusted under 35 U.S.C. 154(b) by 834 days.

(21) Appl. No.: 14/503,636

(22) Filed: Oct. 1, 2014

(65) Prior Publication Data

US 2015/0091569 A1  Apr. 2, 2015

(30) Foreign Application Priority Data

Oct. 1, 2013  (JP) ................. 2013-206488

(51) Int. Cl.
| | | |
|---|---|---|
| *G03G 15/20* | (2006.01) | |
| *A61B 5/055* | (2006.01) | |
| *G01R 33/54* | (2006.01) | |
| *A61B 5/00* | (2006.01) | |
| *G01R 33/483* | (2006.01) | |
| *G01R 33/561* | (2006.01) | |

(52) U.S. Cl.
CPC ............ *A61B 5/055* (2013.01); *G01R 33/543* (2013.01); *A61B 5/0042* (2013.01); *A61B 5/4566* (2013.01); *A61B 2576/026* (2013.01); *G01R 33/4833* (2013.01); *G01R 33/5616* (2013.01)

(58) Field of Classification Search
CPC .............. G01R 33/543; G01R 33/5659; G01R 33/3415; G01R 33/36; A61B 5/055
USPC ........................................... 324/309
See application file for complete search history.

(56) References Cited

U.S. PATENT DOCUMENTS

| | | | |
|---|---|---|---|
| 6,952,097 B2 | 10/2005 | Schreck et al. | |
| 7,548,638 B2 | 6/2009 | Graessner | |
| 8,080,997 B2 | 12/2011 | Kassai | |
| 8,664,955 B1* | 3/2014 | Halpern | 324/316 |
| 8,742,756 B2 | 6/2014 | Wu et al. | |

(Continued)

FOREIGN PATENT DOCUMENTS

| | | |
|---|---|---|
| JP | 2005-125099 | 5/2005 |
| JP | 2005-237968 | 9/2005 |

(Continued)

OTHER PUBLICATIONS

Japanese office action dated May 29, 2018, in Patent Application No. JP 2014-163061.

*Primary Examiner* — Walter L Lindsay, Jr.
*Assistant Examiner* — Frederick Wenderoth
(74) *Attorney, Agent, or Firm* — Nixon & Vanderhye P.C.

(57) ABSTRACT

A magnetic resonance imaging apparatus according to an embodiment includes a receiving unit and a determining unit. The receiving unit collectively receives settings of an imaging region on an image of a subject with respect to at least part of imaging protocols in a series of imaging protocols performed in an examination. The determining unit determines the propriety of the setting with respect to each imaging protocol included in the part of the imaging protocols before imaging is started using the part of the imaging protocols.

13 Claims, 9 Drawing Sheets

(56) References Cited

U.S. PATENT DOCUMENTS

| | | | | |
|---|---|---|---|---|
| 2004/0017195 A1* | 1/2004 | Kassai | ............... | G01R 33/3856 |
| | | | | 324/315 |
| 2011/0052034 A1* | 3/2011 | Watanabe | ................ | A61B 6/00 |
| | | | | 382/132 |
| 2011/0169490 A1* | 7/2011 | Furudate | .............. | G01R 33/543 |
| | | | | 324/309 |
| 2012/0093385 A1* | 4/2012 | Yokosawa | ............ | A61B 5/0037 |
| | | | | 382/131 |

FOREIGN PATENT DOCUMENTS

| | | |
|---|---|---|
| JP | 2009-148463 A | 7/2009 |
| JP | 2010-088872 A | 4/2010 |
| JP | 2012-045192 | 3/2012 |
| WO | 2009/151041 A1 | 12/2009 |

* cited by examiner

MAGNETIC RESONANCE IMAGING APPARATUS AND IMAGING PLANNING METHOD

CROSS-REFERENCE TO RELATED APPLICATIONS

This application is based upon and claims the benefit of priority from Japanese Patent Application No. 2013-206488, filed on Oct. 1, 2013, the entire contents of all of which are incorporated herein by reference.

FIELD

Embodiments described herein relate generally to a magnetic resonance imaging apparatus and an imaging planning method.

BACKGROUND

Conventionally, in an examination using a magnetic resonance imaging apparatus, there are cases where a plurality of imaging protocols are used to image the same slice of a subject. For these cases, a technique is known with which the positioning processes of the slice using the protocols are performed collectively. In imaging using such a technique, it is desired that imaging using each imaging protocol be performed continuously after the positioning of the slice is performed. However, with the conventional technique, before imaging is performed using each of the imaging protocols, a determination may be made on whether the imaging is possible in view of influences on the subject and the image quality. For this reason, there have been cases where imaging using a plurality of protocols is stopped in the middle of the imaging.

DETAILED DESCRIPTION

A magnetic resonance imaging (MRI) apparatus according to an embodiment includes a receiving unit and a determining unit. The receiving unit collectively receives settings of an imaging region on an image of a subject with respect to at least part of imaging protocols in a series of imaging protocols performed in an examination. The determining unit determines the propriety of the setting with respect to each imaging protocol included in the part of the imaging protocols before imaging is started using the part of the imaging protocols.

Embodiments of an MRI apparatus and an imaging planning method are described below in detail with reference to the drawings.

First Embodiment

Figure 1:
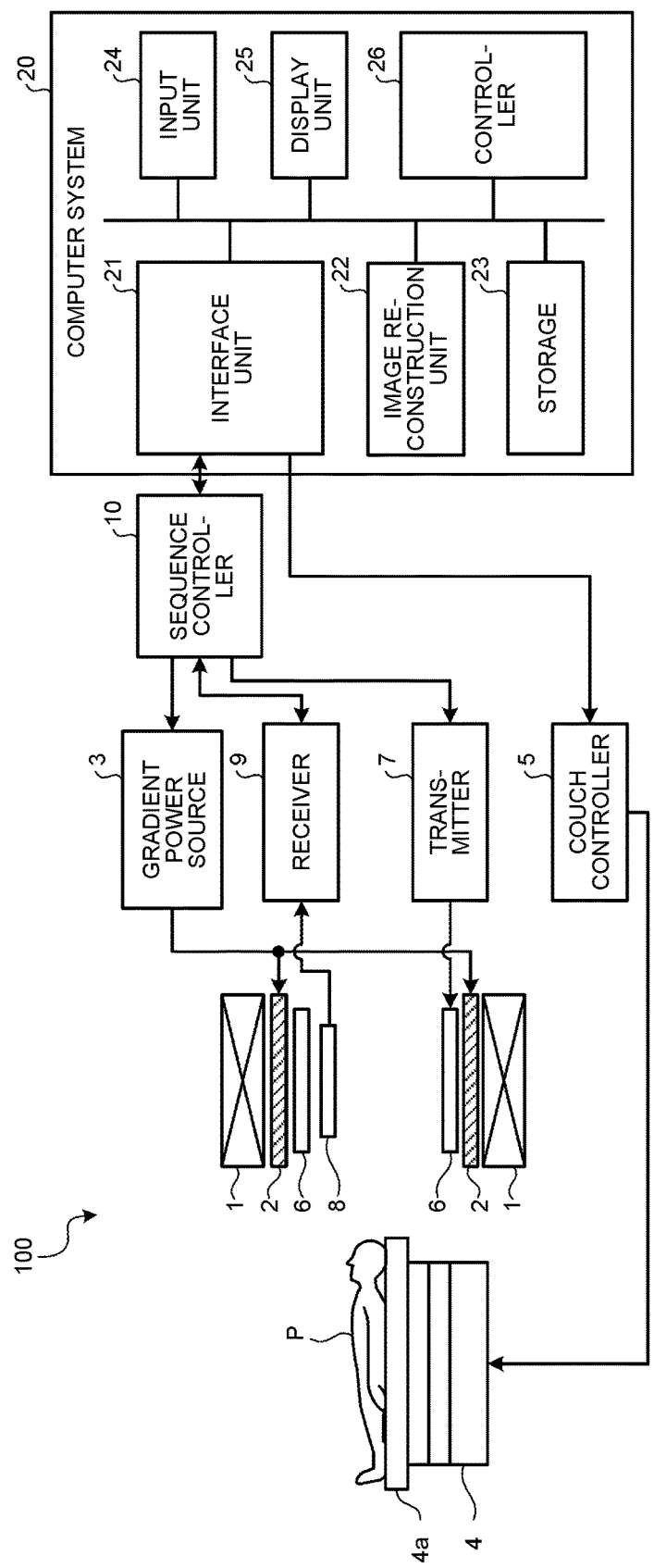
FIG. 1 is a diagram illustrating a configuration of a magnetic resonance imaging (MRI) apparatus according to a first embodiment.

FIG. 1 is a diagram illustrating a configuration of a magnetic resonance imaging (MRI) apparatus according to a first embodiment. As illustrated in FIG. 1, the MRI apparatus 100 includes a static magnetic fields magnet 1, a gradient coil 2, a gradient power source 3, a couch 4, a couch controller 5, a transmission radio frequency (RF) coil 6, a transmitter 7, a receiving RF coil 8, a receiver 9, a sequence controller 10, and a computer system 20.

The static magnetic fields magnet 1 is a magnet formed in a hollow cylindrical shape and generates a uniform static magnetic field in the space inside thereof. As the static magnetic fields magnet 1, a permanent magnet or a superconducting magnet may be used, for example.

The gradient coil 2 is a coil formed in a hollow cylindrical shape and disposed inside the static magnetic fields magnet 1. The gradient coil 2 is formed with three coils combined that correspond to each of the axes x, y, and z, which are orthogonal to one another. These three coils individually receives current supply from the gradient power source 3 described later to generate gradient magnetic fields of which the magnetic field strengths change along each of the axes x, y, and z. The z-axis direction may be the same as the direction of the static magnetic field. The gradient power source 3 supplies current to the gradient coil 2.

The gradient magnetic fields of the axes x, y, and z generated by the gradient coil 2 correspond to, for example, a slice selection gradient magnetic field Gss, a phase encode gradient magnetic field Gpe, and a read-out gradient magnetic field Gro respectively. The slice selection gradient magnetic field Gss is used for arbitrarily selecting a slice. The phase encode gradient magnetic field Gpe is used for changing the phase of a magnetic resonance signal in accordance with the spatial position. The read-out gradient magnetic field Gro is used for changing the frequency of a magnetic resonance signal in accordance with the spatial position.

The couch 4 includes a couchtop 4a on which a subject P is placed. The couchtop 4a is inserted into a hollow (i.e., an opening for imaging) of the gradient coil 2 with the subject P placed thereon under the control of the couch controller 5 described later. Usually, the couch 4 is installed such that the longitudinal direction thereof is parallel with the central axis of the static magnetic fields magnet 1. The couch controller 5 is an apparatus that controls the couch 4 under the control of a controller 26 and drives the couch 4 to move the couchtop 4*a* in the longitudinal and vertical directions.

The transmission RF coil 6 is disposed inside the gradient coil 2 and generates a radio frequency (RF) pulse (high frequency magnetic pulse) with high frequency pulse current supplied from the transmitter 7. The transmitter 7 supplies high frequency pulse current corresponding to the Larmor frequency to the transmission RF coil 6. The receiving RF coil 8 is disposed inside the gradient coil 2 and receives a magnetic resonance signal emitted from the subject P under the influence of the RF pulse described above. Upon receiving a magnetic resonance signal, the receiving RF coil 8 outputs the magnetic resonance signal to the receiver 9.

The receiver 9 generates a magnetic resonance (MR) signal data based on the magnetic resonance signal output from the receiving RF coil 8. The receiver 9 generates the MR signal data through digital conversion of the magnetic resonance signal output from the receiving RF coil 8. The MR signal data is placed in a k space in a manner associated with information of spatial frequencies in the phase encode (PE) direction, in the read-out (RO) direction, and the slice encode (SE) direction by the slice selection gradient magnetic field Gss, the phase encode gradient magnetic field Gpe, and the read-out gradient magnetic field Gro, which have been described above. Upon generating the MR signal data, the receiver 9 transmits the MR signal data to the sequence controller 10.

The sequence controller 10 performs a scan of the subject P by driving the gradient power source 3, the transmitter 7, and the receiver 9 based on sequence execution data transmitted from the computer system 20. The sequence execution data described here is information in which pulse sequences indicating procedures for performing a scan of the subject P are defined, such as the strength of the power source that the gradient power source 3 supplies to the gradient coil 2 and the timing of supplying the power source, the strength of an RF signal that the transmitter 7 transmits to the transmission RF coil 6 and the timing of transmitting the RF signal, and the timing that the receiver 9 detects a magnetic resonance signal. When the MR signal data is transmitted from the receiver 9 after the sequence controller 10 drives the gradient power source 3, the transmitter 7, and the receiver 9 based on the sequence execution data, the sequence controller 10 forwards the transmitted MR signal data to the computer system 20.

The computer system 20 performs overall control of the MRI apparatus 100. For example, the computer system 20 drives each unit included in the MRI apparatus 100 so as to perform a scan of the subject P, image reconstruction, and other similar processing. The computer system 20 includes an interface unit 21, an image reconstruction unit 22, a storage 23, an input unit 24, a display unit 25, and the controller 26.

The interface unit 21 controls inputs and outputs of various signals transmitted to and received from the sequence controller 10. For example, the interface unit 21 transmits sequence execution data to the sequence controller 10 and receives MR signal data from the sequence controller 10. Upon receiving MR signal data, the interface unit 21 stores each piece of the MR signal data in the storage 23 separately for each subject P.

The image reconstruction unit 22 applies postprocessing, that is, reconstruction processing such as Fourier transform on the MR signal data stored by the storage 23 so as to generate spectrum data or image data of a desired nuclear spin in the subject P. The image reconstruction unit 22 also causes the generated spectrum data or image data to be stored in the storage 23 separately for each subject P.

The storage 23 stores therein various data and computer programs necessary for processing performed by the controller 26 described later. For example, the storage 23 stores therein the MR signal data received by the interface unit 21 and the spectrum data and the image data generated by the image reconstruction unit 22 separately for each subject P. The storage 23 may be a semiconductor memory element such as a random access memory (RAM), a read only memory (ROM), or a flash memory or a storage such as a hard disk or an optical disk, for example.

The input unit 24 receives various instructions and information inputs from the operator. As the input unit 24, a pointing device such as a mouse or a trackball, a selection device such as a mode switching switch, or an input device such as a keyboard may be used appropriately.

The display unit 25 displays various types of information such as spectrum data or image data under the control of the controller 26. As the display unit 25, a display device such as a liquid crystal display may be used.

The controller 26 includes a central processing unit (CPU) (not illustrated), a memory, and other similar devices and performs overall control of the MRI apparatus 100. The controller 26 generates various types of sequence execution data based on imaging conditions input by the operator through the input unit 24 and controls the scan by transmitting the generated sequence execution data to the sequence controller 10, for example. The controller 26 also controls the image reconstruction unit 22 to reconstruct an image based on MR signal data when the MR signal data is transmitted from the sequence controller 10 as a result of the scan.

A configuration of the MRI apparatus 100 according to the present embodiment has been described above. Under this configuration, the MRI apparatus 100 has a function to collectively perform the positioning processes of the slice with each of the imaging protocols when a plurality of imaging protocols are used to image the same slice of the subject. In imaging using such a function, it is desired that imaging using each imaging protocol be performed continuously after the positioning of the slice is performed. However, with the conventional technique, before imaging is performed using each of the imaging protocols, a determination may be made on whether the imaging is possible in view of influences on the subject and the image quality. For this reason, there have been cases where imaging using a plurality of protocols is stopped in the middle of the imaging.

In contrast, the MRI apparatus 100 according to the present embodiment calculates an index value related to the influences of imaging on the subject or the image quality with respect to at least one image protocol and compares the calculated index value and a predetermined threshold, thereby determining whether the imaging of the positioned slice is possible, before imaging is performed using each of the imaging protocols. As described above, in the MRI apparatus 100 according to the present embodiment, an imaging possibility determination is made with respect to an imaging protocol with which there is a possibility that the imaging is stopped, before imaging is performed using each of the imaging protocols. With this configuration, when the same slice of the subject is imaged using a plurality of imaging protocols, the imaging using the imaging protocols can be prevented from being stopped in the middle of the imaging.

The MRI apparatus 100 according to the present embodiment includes a receiving unit and a determining unit. In a series of imaging protocols performed in an examination, with respect to at least part of the imaging protocols, the receiving unit collectively receives settings of an imaging region on an image of a subject. The determining unit determines the propriety of the setting of the imaging region with respect to each imaging protocol included in the part of the imaging protocols before imaging is started using the part of the imaging protocols.

In the present embodiment, an example is described in which a slice is set as an imaging region and an example is described in which the positioning of the slice is performed as a setting of the imaging region. Furthermore, in the present embodiment, an example is described in which a determination is made on whether the imaging of the positioned slice is possible as the propriety of the setting of the imaging region.

Figure 2:
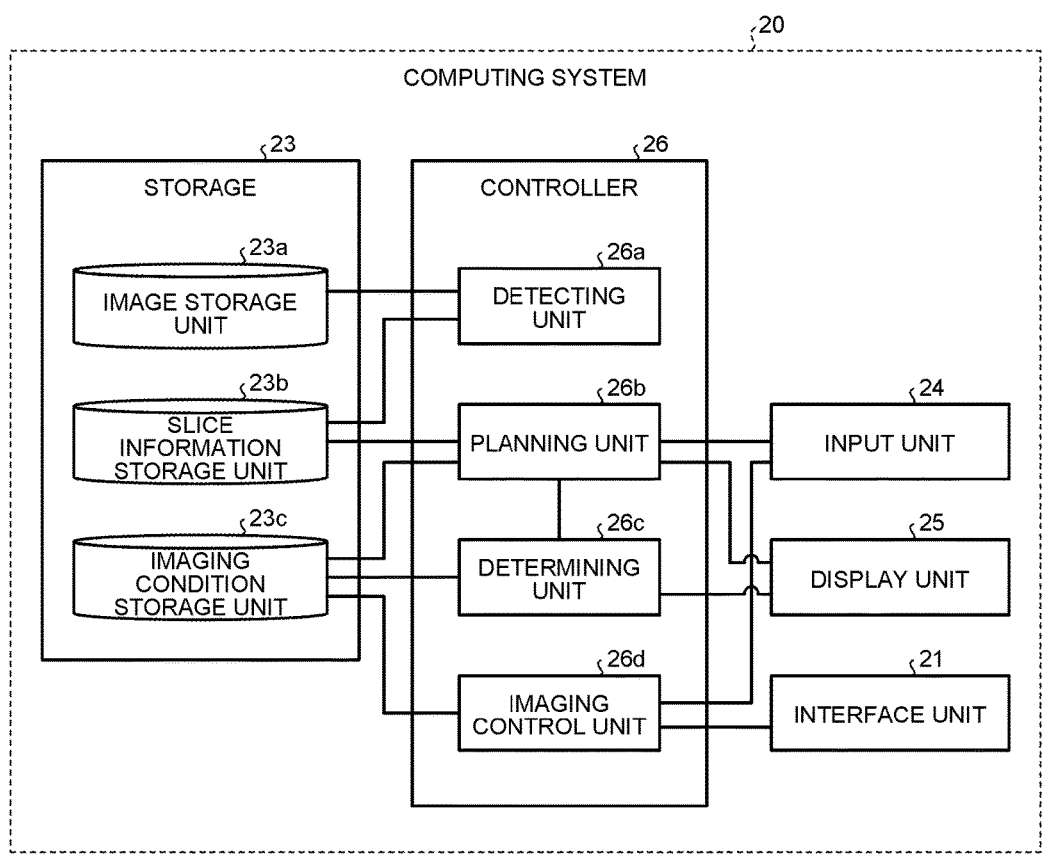
FIG. 2 is a functional block diagram illustrating a detailed configuration of the MRI apparatus according to the first embodiment.

FIG. 2 is a functional block diagram illustrating a detailed configuration of the MRI apparatus 100 according to the first embodiment. In FIG. 2, in various parts included in the computer system 20 illustrated in FIG. 1, the interface unit 21, the storage 23, the input unit 24, the display unit 25, and the controller 26 are presented.

As illustrated in FIG. 2, the storage 23 includes an image storage unit 23a, a slice information storage unit 23b, and an imaging condition storage unit 23c.

The image storage unit 23a stores therein image data generated by the image reconstruction unit 22. For example, the image storage unit 23a stores therein an image for positioning in which the subject is imaged and an image for diagnosis. For example, when the imaging target region is the head, a sagittal image in which the head of the subject is imaged is stored as an image for positioning or an image for diagnosis.

The slice information storage unit 23b stores therein slice information related to a slice detected based on an image of the subject. The slice information described here is information indicating the position, the orientation, the thickness, and the area (length, width) of the slice. For example, the position and the orientation of the slice is represented by a first vector indicating the orientation of the slice and coordinates indicating the starting point of the first vector or a second vector (a vector of which the starting point is a predetermined reference position). Furthermore, information of the thickness and the area of the slice is represented by lengths of three orthogonal directions (x, y, z) when the slice is approximated as a rectangular parallelepiped, for example.

The imaging condition storage unit 23c stores therein imaging conditions related to various imaging methods and pulse sequences for each imaging protocol specified in accordance with the imaging target region and the imaging purpose. The imaging conditions described here include a repetition time (TR), an echo time (TE), the number of matrices, and the position, the orientation, the thickness, and the area of the slice to be imaged. There may be some cases where the slices to be imaged are set in the unit referred to as a slab (also referred to as a slice group) in which a plurality of slices are arranged in the direction of the thickness of each slice. In those cases, the imaging conditions include the number of the slices to be included in one slab, gaps between the slices, and other similar items.

The controller 26 includes a detecting unit 26a, a planning unit 26b, a determining unit 26c, and an imaging control unit 26d. In the present embodiment, the planning unit 26b corresponds to the receiving unit.

The detecting unit 26a detects a slice of the subject based on an image of the subject. When the imaging target region is the head, for example, the detecting unit 26a detects a slice of the brain of the subject based on a sagittal image in which the head of the subject is imaged. In this process, various known methods can be used for detecting a slice. For example, the detecting unit 26a extracts an area of the target region with various types of image processing from an image of the subject to detect a slice related to the extracted area based on the anatomical features and shape of the target region. The detecting unit 26a then causes the slice information storage unit 23b to store therein slice information related to the detected slice.

In the process described above, various types of images can be used for the detection. For example, the images for the detection are the images suitable for the detection processing for detecting the target region and the images acquired through execution of a particular sequence specified in accordance with the detection processing. Alternatively, the image for detection may be an arbitrary image that is generated during a time period, when a plurality of imaging processes are repeated to obtain an image for diagnosis. As another example, when an image acquired at an arbitrary point of time is set as the image for positioning and procedures of deciding the imaging position of the next image to be taken are repeated using the set image for positioning, the set image for positioning may be used as the image for the detection. As a further example, one slice image is generated from a plurality of slice images or pieces of volume data in which an imaging region set in a wide area of the subject is imaged to be used as the image for the detection.

In a series of imaging protocols performed in an examination, with respect to at least part of the imaging protocols, the planning unit 26b collectively receives settings of an imaging region on an image of the subject. In the present embodiment, when a plurality of imaging protocols are used to image the same slice of the subject, the planning unit 26b collectively performs the positioning processes of the slice with each of the imaging protocols. More specifically, when a plurality of imaging protocols are used to image a slice detected by the detecting unit 26a, the planning unit 26b collectively performs the positioning processes of the slice with each of the imaging protocols.

For example, the planning unit 26b receives an operation of selecting a plurality of imaging protocols for imaging the same slice of the subject from imaging protocols stored in the imaging condition storage unit 23c from the operator. In this process, the planning unit 26b receives an operation of selecting a plurality of imaging protocols with different types of imaging sequences, for example. The planning unit 26b then groups the selected imaging protocols and collectively performs the positioning processes of the slice with respect to the grouped imaging protocols in a linked manner.

The planning unit 26b also receives an operation of selecting or changing the slice detected by the detecting unit 26a from the operator. For example, the planning unit 26b causes the display unit 25 to display a graphical user interface (GUI) for imaging planning and receives the operation of selecting or changing the slice from the operator via the GUI. The planning unit 26b then applies the slice selected or changed by the operator to each of the grouped imaging protocols. In this process, the planning unit 26b updates the imaging conditions for each imaging protocol stored in the imaging condition storage unit 23c with the position, the orientation, the thickness, and the area of the slice that has been selected or changed.

Figure 3:
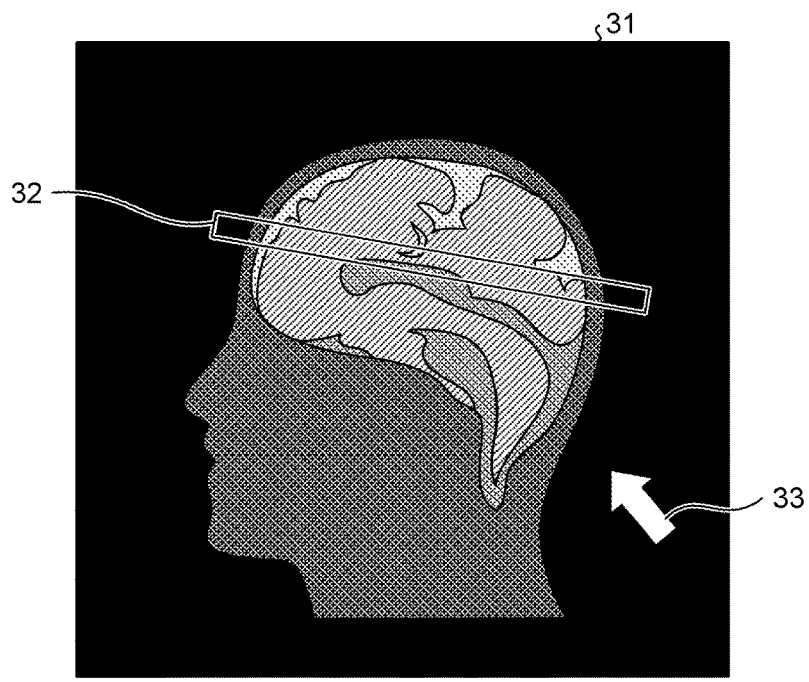
FIG. 3 is a diagram illustrating an example of display of a graphic user interface (GUI) caused by a planning unit according to the first embodiment.

FIG. 3 is a diagram illustrating an example of display of a GUI caused by the planning unit 26b according to the first embodiment. When the imaging target region is the head, for example, the planning unit 26b causes the display unit 25 to display a sagittal image 31 in which the head of the subject is imaged, as illustrated in FIG. 3. The sagittal image 31 displayed in this process may be, for example, an image for detection used by the detecting unit 26a. The image may be an image taken for positioning or an image taken for diagnosis. The planning unit 26b also acquires slice information of the slice detected by the detecting unit 26a from the slice information storage unit 23b and causes a graphic 32 having a rectangular shape and representing the slice to be displayed on the sagittal image 31 based on the acquired slice information. It should be noted that the graphic 32 displayed in this process may present a slab in which a plurality of slices are arranged in the direction of the thickness of each slice. The planning unit 26b recognizes that the slice has been selected when receiving an operation of placing a pointer 33 on the graphic 32 via the input unit 24, for example. Furthermore, the planning unit 26b recognizes that the slice has been changed when receiving an operation of moving the selected graphic 32 or an operation of changing the PE direction within the same slice with respect to the slice corresponding to the selected graphic 32 via the input unit 24, for example.

In a series of imaging protocols performed in an examination, with respect to at least part of the imaging protocols, the determining unit 26c determines the propriety of the setting before imaging is started using the part of the imaging protocols. In the present embodiment, the determining unit 26c calculates an index value related to the influences of imaging on the subject or the image quality with respect to at least one imaging protocol before imaging is performed using the imaging protocols. The determining unit 26c then compares the calculated index value and a predetermined threshold, thereby determining whether the imaging of the slice positioned by the planning unit 26b is possible.

The determining unit 26c determines whether the imaging of the selected or changed slice is possible each time an operation of selecting or changing the slice is received by the planning unit 26b. More specifically, the determining unit 26c determines that the imaging of the slice is possible when the calculated index value is equal to or lower than the threshold, and determines that the imaging of the slice is not possible when the calculated index value exceeds the threshold.

With respect to an imaging protocol using an echo planar imaging (EPI) sequence, for example, it is known that problems become apparent when an oblique slice is imaged, such as the problem that electrical stimulation is caused by an increase in the time rate of change in the magnetic field strength (hereinafter, dB/dt) and the image quality problem that a distortion becomes large. To solve these problems, the determining unit 26c calculates the measure of the angle formed by the RO direction of the slice and the direction of the static magnetic field as an index value, for example.

Furthermore, the determining unit 26c determines whether the imaging of the slice is possible with respect to a particular imaging protocol in a plurality of imaging protocols, for example. The determining unit 26c determines whether the imaging of the slice is possible with respect to an imaging protocol using an EPI sequence, for example. It should be noted that the particular imaging protocol described here is not limited to an imaging protocol using an EPI sequence. For example, when the same slice is imaged using a plurality of imaging protocols, an imaging possibility determination has to be made with some imaging protocols but not with other imaging protocols, depending on the type of the imaging sequence and imaging conditions. The determining unit 26c thus makes an imaging possibility determination with respect to an imaging protocol that has been prespecified as requiring an imaging possibility determination out of the imaging protocols. In this process, for example, the determining unit 26c refers to a determination necessity flag preset for each imaging protocol as a part of the imaging conditions to determine whether an imaging possibility determination has to be made. For example, an EPI sequence of a diffusion weighted image (DWI) is specified as requiring an imaging possibility determination and a $T_1$-weighted image sequence, $T_2$-weighted image sequence, and a fluid attenuated inversion recovery (FLAIR) sequence are specified as not requiring an imaging possibility determination.

Furthermore, even in the case of an imaging protocol requiring an imaging possibility determination, for example, the determination criteria may be different depending on the type of the imaging sequence and the imaging conditions. For this reason, the determining unit 26c uses different thresholds in accordance with the type of the imaging sequence and the imaging conditions used in the imaging protocol, for example. Even in the case of an EPI sequence of a DWI specified as requiring an imaging possibility determination, the measure of the angle as a threshold may be set to 5° in some cases and set to 10° in other cases, depending on the imaging conditions, for example. This threshold is stored in advance in the imaging condition storage unit 23c for each imaging protocol as a part of the imaging conditions and acquired from the imaging condition storage unit 23c when an imaging possibility determination is made by the determining unit 26c, for example.

As described above, in a series of imaging protocols performed in an examination, with respect to at least part of the imaging protocols, the planning unit 26b collectively receives settings of an imaging region on an image of the subject. In this process, the series of imaging protocols performed in an examination may include an imaging protocol with which a preparation scan and a main scan are performed sequentially. Furthermore, there are some cases where in each of the preparation scan and the main scan, a plurality of scanning processes are sequentially performed.

In such cases, in a plurality of scanning processes included in the series of imaging protocols, with respect to at least part of the scanning processes, the planning unit 26b collectively receives settings of an imaging region. In this process, a scan for detecting an imaging region of the subject can be performed at an arbitrary timing as long as the timing is before a scan of an imaging protocol requiring a determination of the propriety of the imaging region setting in the series of imaging protocols.

In an examination of the head, for example, the following scans may be sequentially performed as preparation scans; a map scan for collecting a sensitivity map presenting a sensitivity distribution of a plurality of coil elements included in the receiving RF coil 8 and a shimming scan for obtaining the value of the current running in a correction coil (not illustrated in FIG. 1) to adjust the uniformity of the static magnetic field. As main scans, the following scans may be sequentially performed; a scan for imaging a $T_1$-weighted image, a scan for imaging a $T_2$-weighted image, a first scan using an EPI sequence for imaging a DWI image, a second scan similarly using an EPI sequence for imaging a DWI image but using different imaging conditions from the first scan, and a scan for collecting volume data of an axial image using a 3D sequence. As a scan for detection in the case as described above, a scan for detecting a slice intersecting an AC-PC line connecting the top limit of the anterior commissure and the bottom limit of the posterior commissure, for example.

In the case described above, with respect to each scan included in the preparation scans and the scan using a 3D sequence included in the main scans, for example, no determination of the propriety of the imaging region will have to be made because those scans are not aimed to image a slice detected by a scan for detection. Furthermore, with respect to the scan for a $T_1$-weighted image and the scan for a $T_2$-weighted image included in the main scans, for example, no determination of the propriety of the imaging region will have to be made because the possibilities of the electrical stimulation problem and the image quality problem are low.

In the case described above, the planning unit 26b collectively receives settings of the imaging conditions with respect to the first scan and the second scan using EPI sequences, for example. In this case, the scan for detection is performed at least before the first scan using an EPI sequence is started. The scan for detection is performed before the preparation scans are started, for example. Alternatively, the scan for detection may be performed between the preparation scans and the main scans, for example.

Furthermore, the determining unit 26c causes the display unit 25 to display information for identifying an imaging protocol with which imaging has been determined as impossible. In this process, the determining unit 26c further causes display of information indicating the difference between an index value and a threshold with respect to an imaging protocol with which imaging has been determined as impossible. The determining unit 26c further causes display of information serving as a guide to enable imaging using an imaging protocol with which imaging has been determined as impossible.

Figure 4:
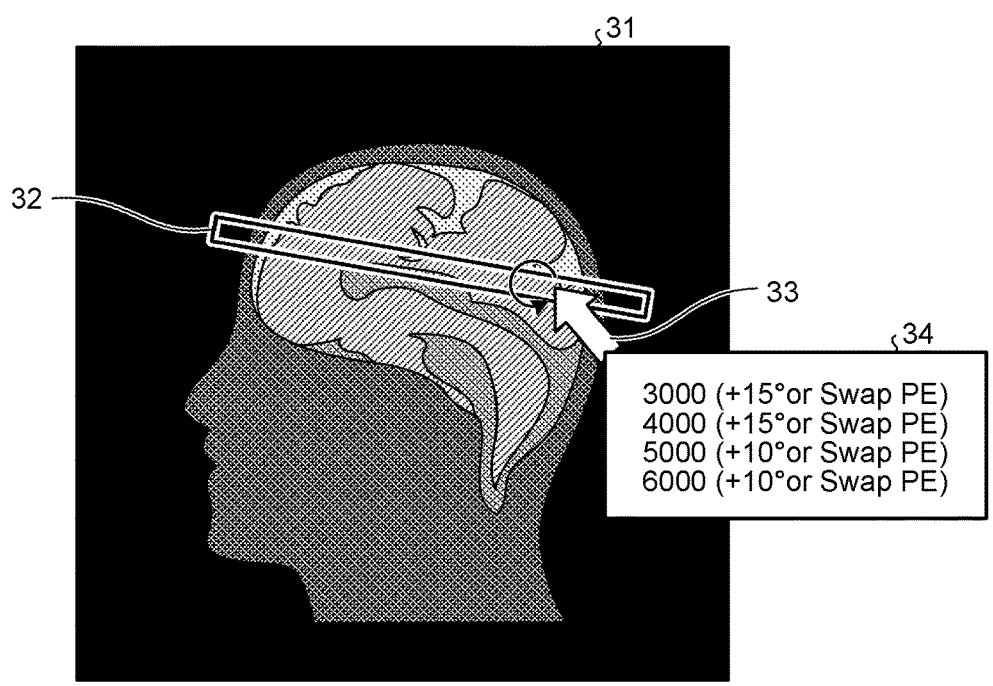
FIG. 4 is a diagram illustrating an example of display of information caused by a determining unit according to the first embodiment.

FIG. 4 is a diagram illustrating an example of display of information caused by the determining unit 26c according to the first embodiment. For example, the determining unit 26c causes display of an NG list 34 listing information related to an imaging protocol with which imaging has been determined as impossible with respect to a slice selected by the operator, as illustrated in FIG. 4. For example, in the NG list 34 illustrated in FIG. 4, each of "3000", "4000", "5000", and "6000" indicates the ID of such an imaging protocol. Furthermore, "(+15° or Swap PE)" indicates that with respect to the imaging protocol with the ID "3000", the difference between the angle formed by the RO direction and the direction of the static magnetic field as an index value and an allowable angle as a threshold is +15° and the guide to enable imaging is swapping the PE direction and the RO direction.

In the example illustrated in FIG. 4, for example, when the operator inclines the angle of the slice by −10° by operating the graphic 32 or replacing the PE direction of the slice with the RO direction, the measure of the angle formed by the RO direction of the slice and the direction of the static magnetic field becomes equal to or lower than the threshold. This changes the state of the NG list 34 to that in which the imaging protocols with the IDs "5000" and "6000" have disappeared and only the imaging protocols with the IDs "3000" and "4000" are displayed. If imaging is performed in this state, imaging is not stopped with imaging protocols other than the imaging protocols with the IDs "3000" and "4000".

When the operator further inclines the angle of the slice by −5° from this state by operating the graphic 32, the imaging protocols with the IDs "3000" and "4000" also disappear from the NG list 34. If imaging is performed in this state, imaging is not stopped with any imaging protocols.

The imaging control unit 26d controls the sequence controller 10 to continuously perform each imaging protocol for which the positioning process of the slice has been performed by the planning unit 26b. More specifically, the imaging control unit 26d receives an instruction from the operator to perform a plurality of imaging protocols grouped by the planning unit 26b via the input unit 24. The imaging control unit 26d then generates sequence execution data with reference to the imaging conditions of each imaging protocol stored in the imaging condition storage unit 23c with respect to each of the imaging protocols for which a performance instruction has been issued. Thereafter, the imaging control unit 26d transmits each piece of the generated sequence execution data to the sequence controller 10 via the interface unit 21, thereby performing imaging using each imaging protocol.

Figure 5:
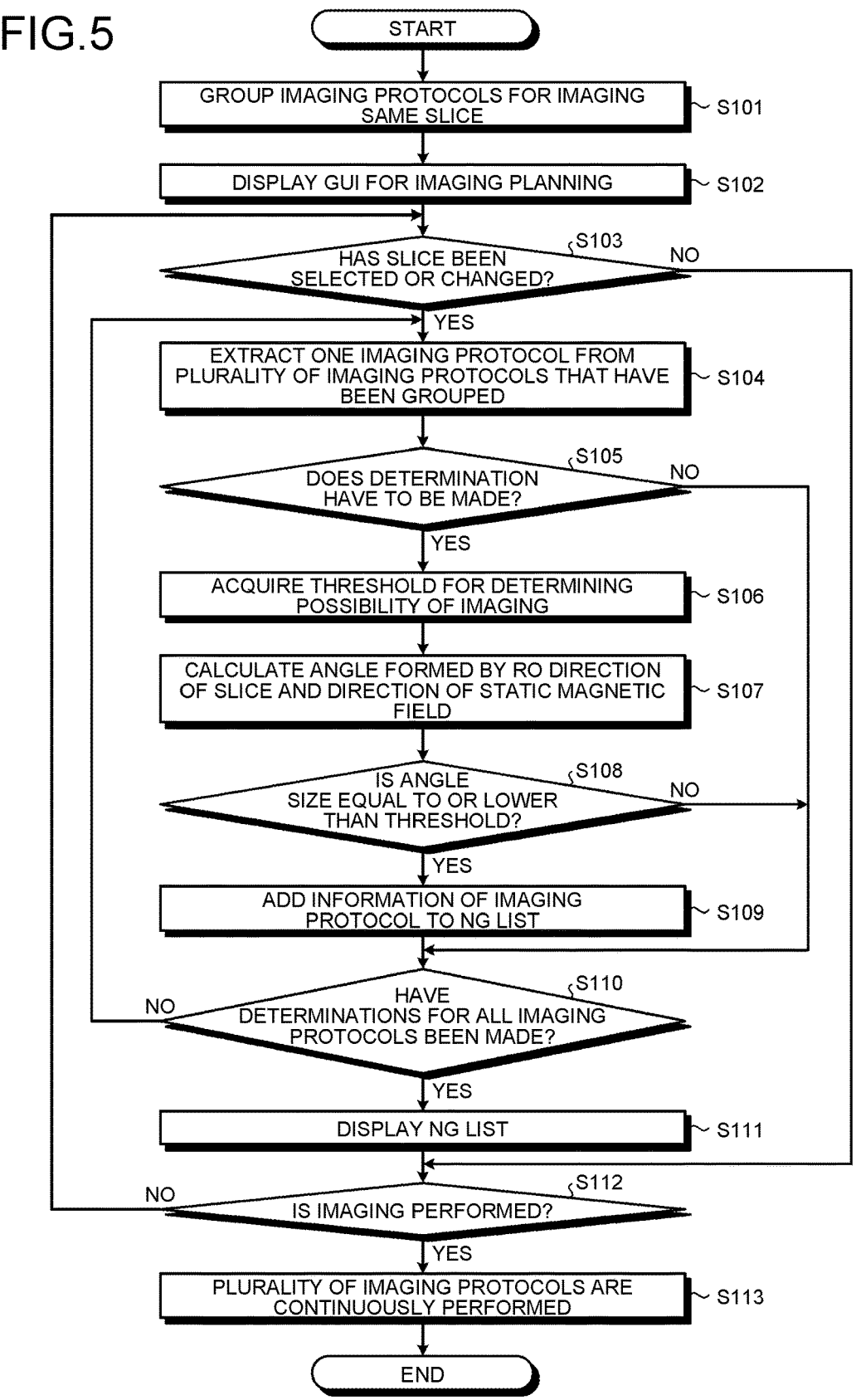
FIG. 5 is a flowchart illustrating a flow of imaging processing performed by the MRI apparatus according to the first embodiment.

FIG. 5 is a flowchart illustrating a flow of imaging processing performed by the MRI apparatus 100 according to the first embodiment. As illustrated in FIG. 5, in the MRI apparatus 100 according to the present embodiment, the planning unit 26b firstly receives an operation of selecting a plurality of imaging protocols for imaging the same slice from the operator and groups the imaging protocols selected by the operator (Step S101).

The planning unit 26b subsequently causes the display unit 25 to display a GUI for imaging planning in accordance with a request from the operator (Step S102). The planning unit 26b also receives an operation of selecting or changing a slice from the operator via the GUI for imaging planning (Step S103). When the operation of selecting or changing the slice is received by the planning unit 26b (Yes at Step S103), the determining unit 26c determines whether the imaging of the slice is possible with respect to a particular imaging protocol in the imaging protocols grouped by the planning unit 26b.

More specifically, the determining unit 26c firstly extracts one imaging protocol from the grouped imaging protocols (Step S104). The determining unit 26c then determines whether an imaging possibility determination has to be made with respect to the extracted imaging protocol (Step S105). In this process, when an imaging possibility determination has to be made (Yes at Step S105), the determining unit 26c acquires a threshold for making an imaging possibility determination of the imaging protocol from the imaging condition storage unit 23c (Step S106).

The determining unit 26c subsequently calculates the angle formed by the RO direction of the slice and the direction of the static magnetic field (Step S107) and determines whether the measure of the calculated angle is equal to or lower than the threshold (Step S108). Thereafter, when the measure of the angle is equal to or lower than the threshold (Yes at Step S108), the determining unit 26c adds information of the imaging protocol to the NG list (Step S109).

Thereafter, the determining unit 26c determines whether imaging possibility determinations have been made with respect to all the grouped imaging protocols (Step S110). It should be noted that when an imaging possibility determination does not have to be made (No at Step S105) or when the measure of the angle is larger than the threshold (No at Step S108), the determining unit 26c does not add information of the imaging protocol to the NG list and determines whether imaging possibility determinations have been made with respect to all the grouped imaging protocols (Step S110).

Until the determining unit 26c makes imaging possibility determinations with respect to all the grouped imaging protocols (No at Step S110), the determining unit 26c repeats the processing from Step S104 to Step S109 as described above. Furthermore, when the determining unit 26c has made imaging possibility determinations with respect to all the grouped imaging protocols (Yes at Step S110), the determining unit 26c causes the display unit 25 to display the NG list (Step S111). It should be noted that until the operation of selecting or changing the slice is received by the planning unit 26b (No at Step S103), the determining unit 26c does not perform the processing from Step S104 to Step S111 described above but waits.

Thereafter, until an instruction to perform imaging is received by the imaging control unit 26d (No at Step S112), the planning unit 26b receives the operation of selecting or changing the slice from the operator via the GUI for imaging planning (Step S103). Furthermore, when the slice has been selected or changed by the operator (Yes at Step S103), the determining unit 26c makes an imaging possibility determination with respect to the grouped imaging protocols (Step S104 to Step S111). Furthermore, when an instruction to perform imaging is received by the imaging control unit 26d (Yes at Step S112), the imaging control unit 26d continuously performs the grouped imaging protocols (Step S113).

As described above, in the MRI apparatus 100 according to the present embodiment, each time a slice is selected or changed by the operator via the GUI for imaging planning, an imaging possibility determination is made for each imaging protocol and information related to an imaging protocol with which imaging has been determined as impossible is displayed. With this configuration, when there is an imaging protocol with which imaging is stopped, the operator can be prompted to correct the imaging protocol.

When the planning unit 26b receives an operation of changing the grouping of imaging protocols from the operator, the planning unit 26b performs grouping of the imaging protocols again. The determining unit 26c then performs processing at Step S102 to Step S106 described above, thereby acquiring a threshold for making an imaging possibility determination with respect to an imaging protocol requiring an imaging possibility determination in the newly grouped imaging protocols. With this configuration, even when a plurality of imaging protocols imaging the same slice have been changed, an imaging possibility determination of each imaging protocol after the change can be made.

As described above, in the MRI apparatus 100 according to the first embodiment, an imaging possibility determination is made with respect to an imaging protocol with which there is a possibility that the imaging is stopped, before imaging is performed using each of the imaging protocols. With this configuration, when the same slice of the subject is imaged using a plurality of imaging protocols, the imaging using the imaging protocols can be prevented from being stopped in the middle of the imaging. As a result, the same slice of the subject can be easily imaged using a plurality of imaging protocols, for example, whereby improvement of the diagnosis quality is expected.

Modification of First Embodiment

In the first embodiment described above, an example is described in which the imaging target region is the head, but the imaging target is not limited to the head. For example, when the imaging target region is an intervertebral disk, the same embodiment can be performed.

In this case, the detecting unit 26a detects a plurality of slices of the subject based on an image of the subject. For example, the detecting unit 26a detects a slice of each of a plurality of intervertebral disks included in the spine based on a sagittal image in which the spine of the subject is imaged. In this process, various known methods can be used for detecting a slice.

The detecting unit 26a detects the slices of the intervertebral disks with a method using a plurality of sagittal images of the subject, for example. With this method, the detecting unit 26a extracts a spinal region from each of a plurality of sagittal images that is parallel with a sagittal slice including an intervertebral disk and the spinal canal of the subject and includes at least the intervertebral disk. The detecting unit 26a extracts a two-dimensional intervertebral disk region from each of a plurality of spinal regions that have been extracted. The detecting unit 26a further extracts a three-dimensional intervertebral disk region extending over a plurality of sagittal images based on the two-dimensional intervertebral disk regions that have been extracted. The detecting unit 26a then detects a slice parallel with an intervertebral disk and including the intervertebral disk based on the extracted three-dimensional intervertebral disk region.

Furthermore, when each of the slices detected by the detecting unit 26a is imaged using a plurality of imaging protocols, the planning unit 26b collectively performs the positioning process of each of the slices with each imaging protocol. Also in this case, for example, the planning unit 26b receives an operation of selecting a plurality of imaging protocols for imaging the same slice of the subject out of imaging protocols stored in the imaging condition storage unit 23c from the operator. The planning unit 26b then groups the selected imaging protocols and collectively performs the positioning processes of the slice with respect to the grouped imaging protocols in a linked manner.

The planning unit 26b also receives an operation of selecting or changing the slice detected by the detecting unit 26a from the operator. Also in this case, for example, the planning unit 26b causes the display unit 25 to display a plan GUI for imaging planning and receives the operation of selecting or changing the slice from the operator via the GUI. The planning unit 26b then applies the slice selected or changed by the operator to each of the grouped imaging protocols. In this process, the planning unit 26b updates the imaging conditions for each imaging protocol stored in the imaging condition storage unit 23c with the position, the orientation, the thickness, and the area of the slice that has been selected or changed.

Figure 6:
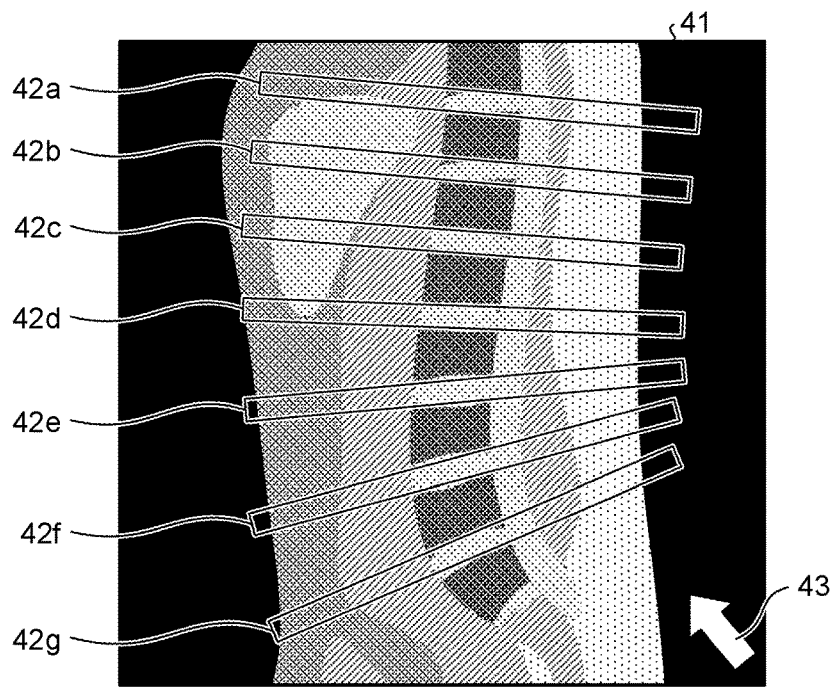
FIG. 6 is a diagram illustrating an example of display of a GUI caused by a planning unit according to a modification of the first embodiment.

FIG. 6 is a diagram illustrating an example of display of a GUI caused by the planning unit 26b according to the modification of the first embodiment. As illustrated in FIG. 6, when the imaging target region is an intervertebral disk, the planning unit 26b causes the display unit 25 to display a sagittal image 41 in which the spine of the subject is imaged, for example. The sagittal image 41 displayed in this process may be, for example, an image for detection used by the detecting unit 26a. The image may be an image taken for positioning or an image taken for diagnosis. The planning unit 26b also acquires slice information of the slices detected by the detecting unit 26a from the slice information storage unit 23b and causes display of graphics 42a to 42g having rectangular shapes and representing the slices on the sagittal image 41 based on the acquired slice information. It should be noted that each of the graphics 42a to 42g may present a slab in which a plurality of slices are arranged in the direction of the thickness of each slice. When the planning unit 26b has received an operation of placing a pointer 43 on any one of the graphics 42a to 42g via the input unit 24, the planning unit 26b recognizes that the slice corresponding to the graphic has been selected, for example. Furthermore, the planning unit 26b recognizes that the slice has been changed when receiving an operation of moving the selected graphic or an operation of changing the PE direction within the same slice with respect to the slice corresponding to the selected graphic via the input unit 24, for example.

Furthermore, before imaging is performed using a plurality of imaging protocols, with respect to at least one of the imaging protocols, the determining unit 26c determines whether imaging is possible for each of a plurality of slices. The determining unit 26c determines whether the imaging of the selected or changed slice is possible each time an operation of selecting or changing the slice is received by the planning unit 26b.

In this case, the determining unit 26c calculates an index value related to the influences of imaging on the subject or the image quality with respect to the slice selected or changed by the operator, similarly to the first embodiment described above. The determining unit 26c also compares the calculated index value and a predetermined threshold, thereby determining whether the imaging of the slice positioned by the planning unit 26b is possible, similarly to the first embodiment described above.

Furthermore, the determining unit 26c causes the display unit 25 to display information for identifying an imaging protocol with which imaging has been determined as impossible, similarly to the first embodiment described above. The determining unit 26c further causes display of information indicating the difference between an index value and a threshold with respect to an imaging protocol with which imaging has been determined as impossible, as well as information serving as a guide to enable imaging using the imaging protocol, similarly to the first embodiment described above.

Figure 7:
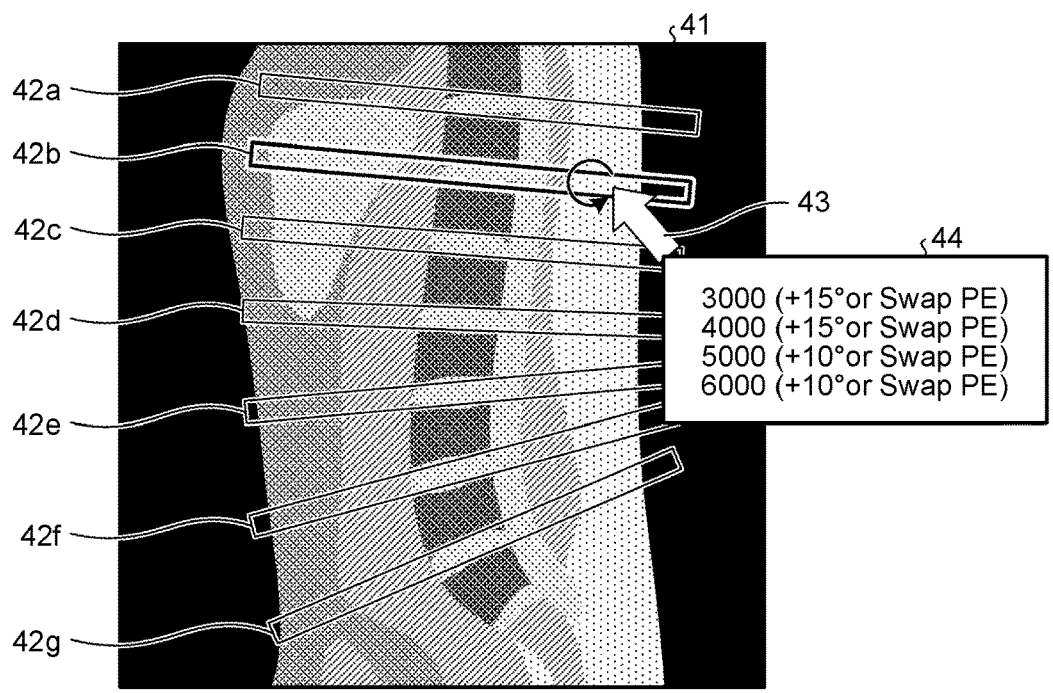
FIG. 7 is a diagram illustrating an example of display of information caused by a determining unit according to the modification of the first embodiment.

FIG. 7 is a diagram illustrating an example of display of information caused by the determining unit 26c according to the modification of the first embodiment. It should be noted that the example illustrated in FIG. 7 presents a case where the slice corresponding to the graphic 42b is selected by the operator, out of the slices respectively corresponding to the graphics 42a to 42g. In this case, as illustrated in FIG. 7, for example, the determining unit 26c causes display of an NG list 44 listing information related to an imaging protocol with which imaging has been determined as impossible with respect to the slice corresponding to the graphic 42b, similarly to the first embodiment described above. It should be noted that even when another slice is selected or changed, the determining unit 26c similarly makes an imaging possibility determination and causes display of the NG list 44 listing information related to an imaging protocol with which imaging has been determined as impossible.

Although an example in which the imaging target region is an intervertebral disk is described here, a similar embodiment can be performed even when the imaging target region is a centrum. When a wide range such as a lower limb is imaged, there are some cases where a plurality of different regions (an iliac region, a femoral region, and a calf region, for example) are imaged with the couchtop moved, on which the subject is placed. In such cases, with respect to the regions included in the imaging range, a slice is detected for each region for the setting of slices in accordance with the shape and the orientation of the region. Even in such cases, before imaging is performed using a plurality of imaging protocols, with respect to each of a plurality of slices that have been detected, the determining unit 26c can determine whether the imaging of the slice is possible.

When the spine or a joint is imaged, for example, there are some cases where an oblique slice is imaged using an EPI sequence. For example, there are some cases where in a local area of an intervertebral foramen or a joint having a disease such as hernia, an oblique slice is imaged with the running nerves, tendons, and/or muscle fibers as the imaging targets. Even in such cases, before imaging is performed using a plurality of imaging protocols, with respect to each of a plurality of oblique slices that has been set, the determining unit 26c can determine whether the imaging of the slice is possible.

Second Embodiment

Next, a second embodiment will be described. In the second embodiment, an example will be described in which a plurality of basic slices are automatically detected based on an image of the subject as a method of detecting a slice. The basic slices described here include an axial slice, a sagittal slice, and a coronal slice, for example. It should be noted that the configuration of an MRI apparatus according to the second embodiment is basically the same as that illustrated in FIG. 1 and FIG. 2 except that processing performed by the detecting unit 26a, the planning unit 26b, and the determining unit 26c is different. For this reason, the processing performed by the detecting unit 26a, the planning unit 26b, and the determining unit 26c according to the present embodiment will be mainly described below.

The detecting unit 26a detects a plurality of slices of the subject based on an image of the subject. For example, the detecting unit 26a detects an axial slice, a sagittal slice, and a coronal slice of the head based on a three-dimensional image (volume data or multi-slice data) in which the head of the subject is imaged. In this process, as a method for detecting each slice, various known methods can be used. For example, the detecting unit 26a extracts an area of the target region with various types of image processing from an image of the subject to detect the orientations and the positions of the axial slice, the sagittal slice, and the coronal slice based on the anatomical features and shape of the target region.

Furthermore, when each of the slices detected by the detecting unit 26a is imaged using a plurality of imaging protocols, the planning unit 26b collectively performs the positioning process of each of the slices with each imaging protocol. For example, when imaging the axial slice detected by the detecting unit 26a using a plurality of protocols, the planning unit 26b collectively performs the positioning processes of the axial slice with each of the imaging protocols. Similarly, the planning unit 26b collectively performs the positioning processes of the sagittal slice and the coronal slice with each imaging protocol.

The planning unit 26b also receives an operation of selecting or changing the slice detected by the detecting unit 26a from the operator. For example, the planning unit 26b causes the display unit 25 to display a GUI for adjusting the detection result and receives the operation of selecting or changing the slice from the operator via the GUI. The planning unit 26b then applies the slice selected or changed by the operator to each of the imaging protocols. In this process, the planning unit 26b updates the imaging conditions for each imaging protocol stored in the imaging condition storage unit 23c with the position, the orientation, the thickness, and the area of the slice that has been selected or changed.

Figure 8:
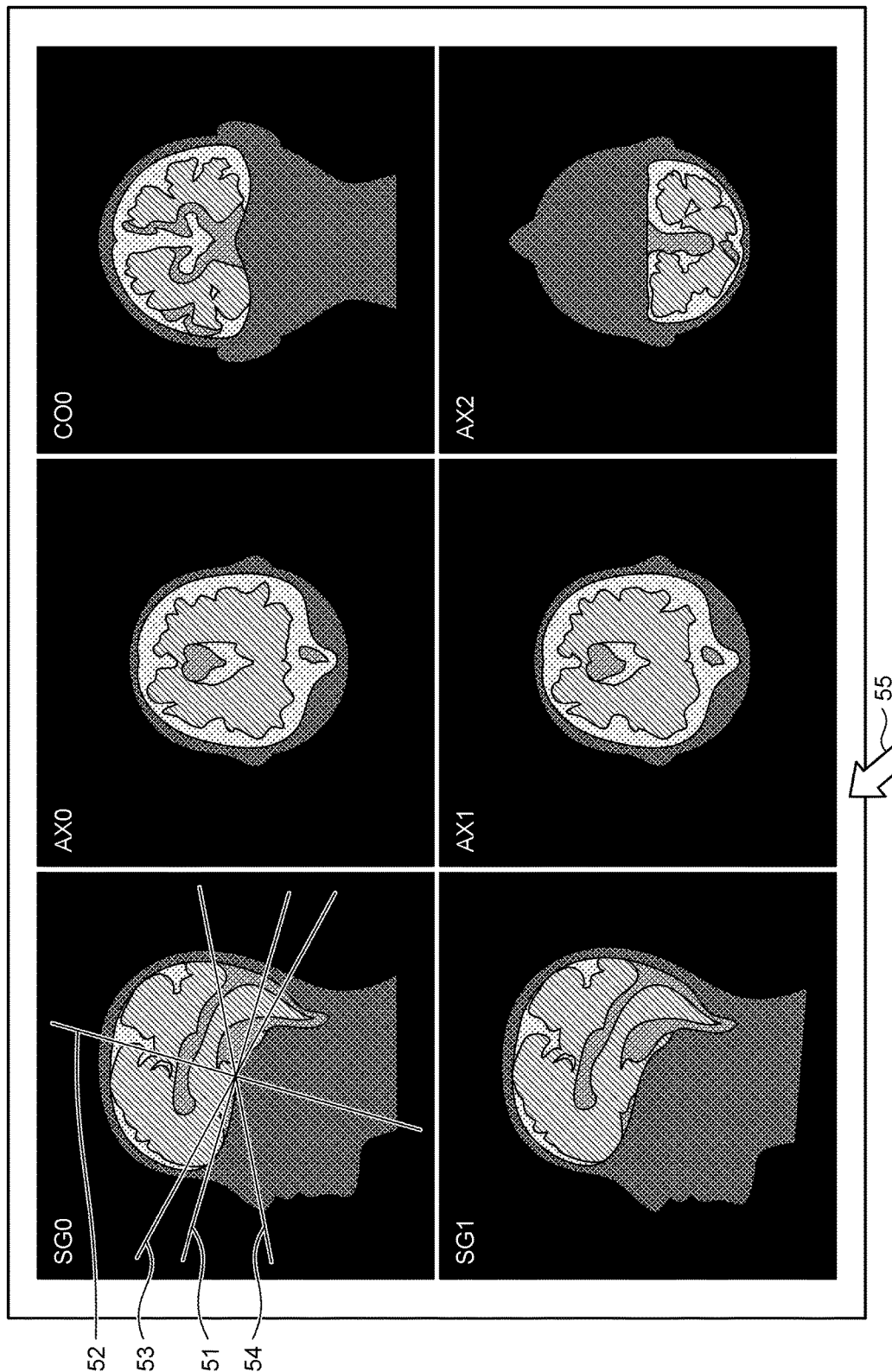
FIG. 8 is a diagram illustrating an example of display of a GUI caused by a planning unit according to a second embodiment.

FIG. 8 is a diagram illustrating an example of display of a GUI caused by the planning unit 26b according to the second embodiment. As illustrated in FIG. 8, the planning unit 26b acquires slice information of an axial slice, a sagittal slice, and a coronal slice detected by the detecting unit 26a from the slice information storage unit 23b, generates an MPR image for each slice based on the acquired slice information, and causes the display unit 25 to display the generated MPR images, for example. In FIG. 8, a slice SG0 is a sagittal slice, a slice AX0 is an axial slice, and a slice CO0 is a coronal slice. Furthermore, in FIG. 8, a graphic 51 displayed on the slice SG0 indicates the position of the slice AX0 and a graphic 52 indicates the position of the slice CO0.

The planning unit 26b also receives an operation of setting another slice based on each of the displayed slices. For example, the planning unit 26b receives an operation of setting a slice obtained by rotating the slice SG0 within the same slice. In this case, as illustrated in FIG. 8, the planning unit 26b causes the display unit 25 to display a slice SG1 obtained by rotating the slice SG0, for example. The planning unit 26b also receives operations of setting graphics 53 and 54 each indicating the position of a slice on the slice SG0. In this case, as illustrated in FIG. 8, the planning unit 26b causes the display unit 25 to display a slice AX1 being the MPR image of an axial slice corresponding to the position of the graphic 53 and a slice AX2 being the MPR image of an axial slice corresponding to the position of the graphic 54, for example. It should be noted that each time the position of any of the graphics 51 to 54 has been changed by the operator, the planning unit 26b causes the display unit 25 to display an MPR image of a slice corresponding to the position after the change.

Furthermore, the planning unit 26b receives an operation of selecting each of the displayed slices from the operator. For example, when receiving an operation of placing a pointer 55 on any one of the displayed slices via the input unit 24, the planning unit 26b recognizes that the slice on which the pointer 55 is placed has been selected.

Furthermore, before imaging is performed using a plurality of imaging protocols, with respect to at least one of the imaging protocols, the determining unit 26c determines whether imaging is possible for each of a plurality of slices. The determining unit 26c determines whether imaging of the selected slice is possible each time an operation of selecting the slice is received by the planning unit 26b.

In this case, the determining unit 26c calculates an index value related to the influences of imaging on the subject or the image quality with respect to the slice selected by the operator, similarly to the first embodiment described above. The determining unit 26c also compares the calculated index value and a predetermined threshold, thereby determining whether the imaging of the slice positioned by the planning unit 26b is possible, similarly to the first embodiment described above.

Furthermore, the determining unit 26c causes the display unit 25 to display information for identifying an imaging protocol with which imaging has been determined as impossible, similarly to the first embodiment described above. The determining unit 26c further causes display of information indicating the difference between an index value and a threshold with respect to an imaging protocol with which imaging has been determined as impossible, as well as information serving as a guide to enable imaging using the imaging protocol, similarly to the first embodiment described above.

Figure 9:
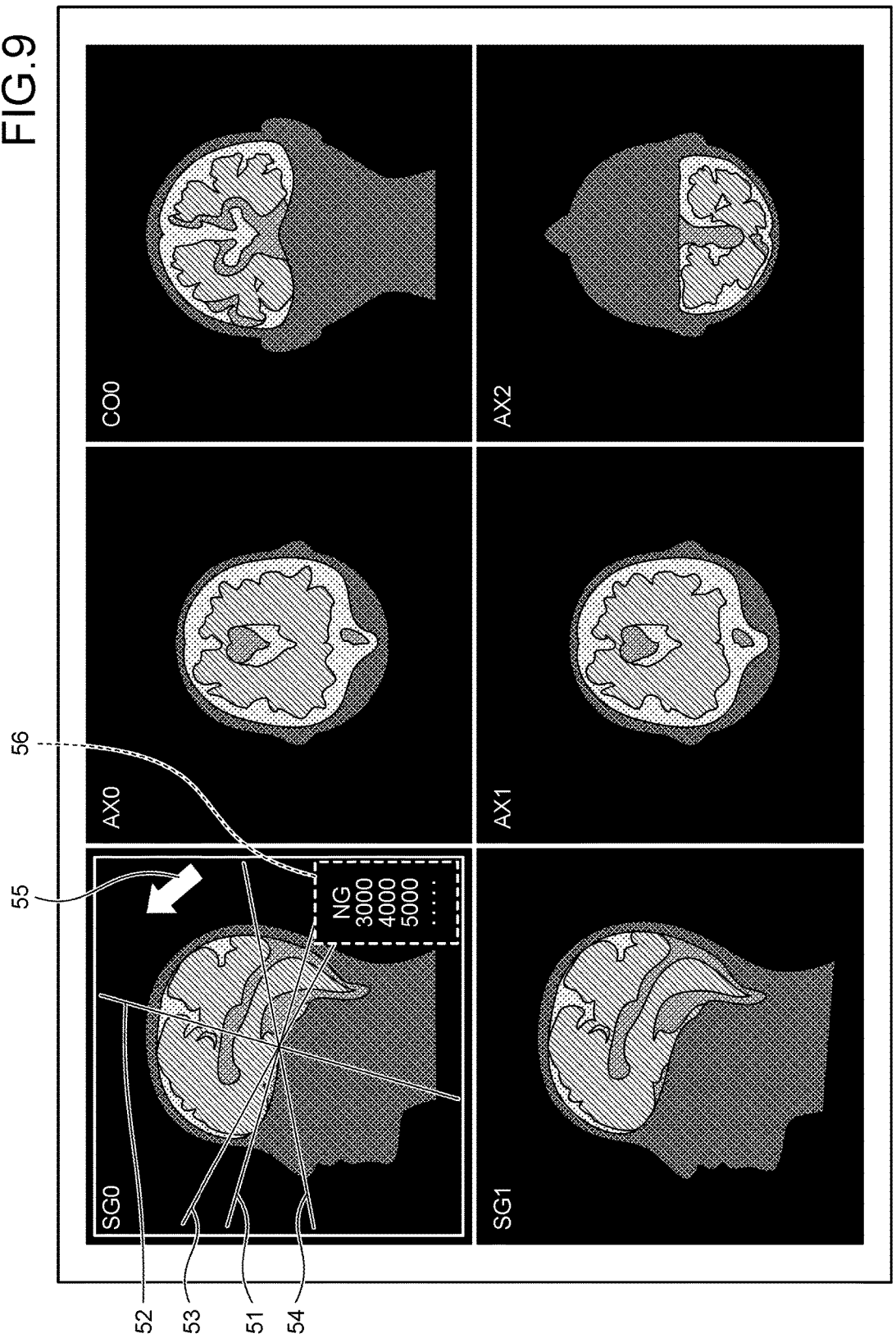
FIGS. 9 and 10 are diagrams illustrating examples of display of information caused by a determining unit according to the second embodiment.
Figure 10:
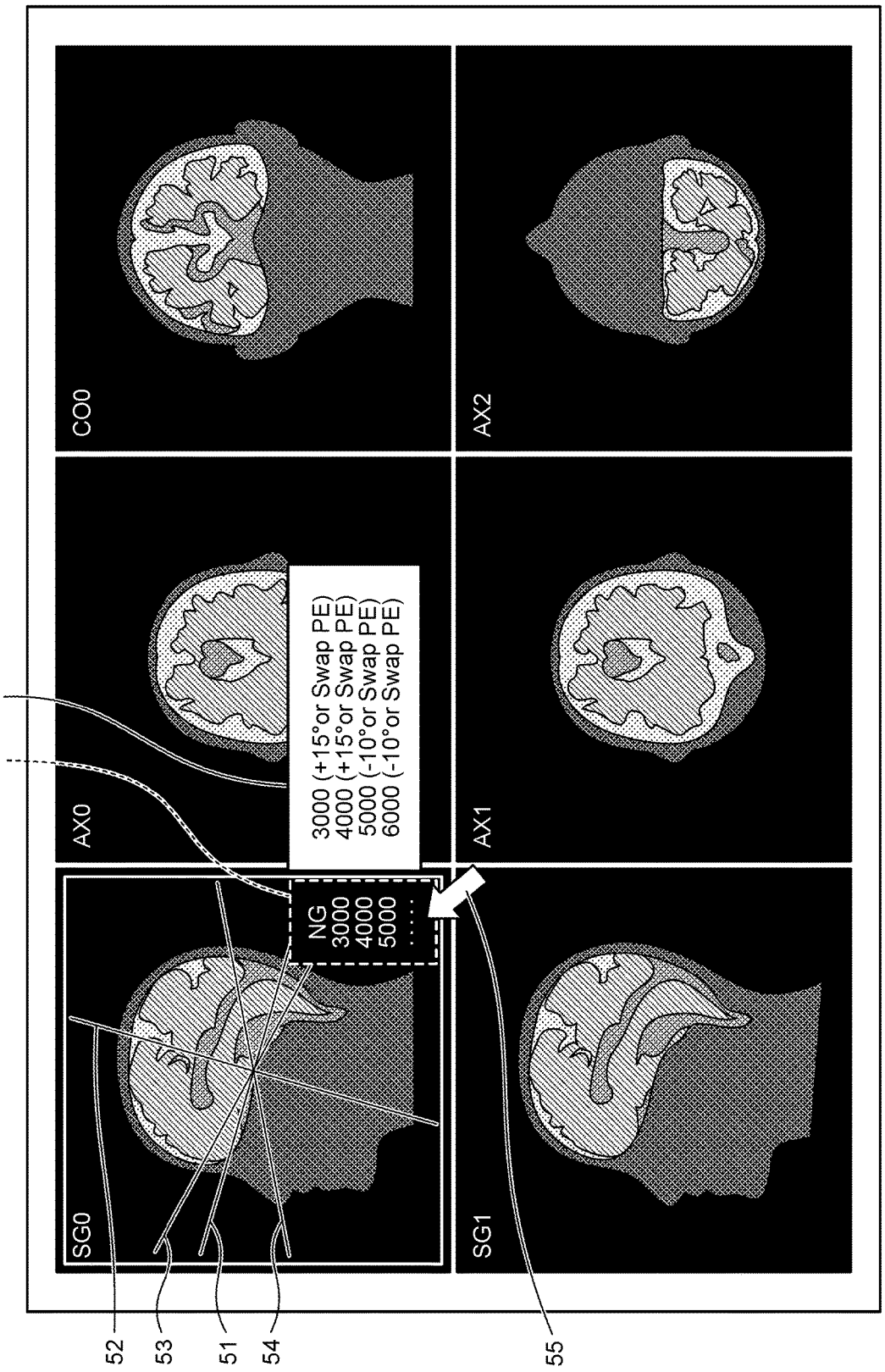

FIGS. 9 and 10 are diagrams illustrating examples of display of information caused by the determining unit 26c according to the second embodiment. It should be noted that the examples illustrated in FIGS. 9 and 10 are cases where the slice SG0 is selected by the operator. As illustrated in FIG. 9, the determining unit 26c causes display of the ID of an imaging protocol with which imaging has been determined as impossible in an NG information region 56 specified on the slice SG0 with respect to the slice SG0 selected by the operator, for example. In this process, when all such IDs cannot be displayed on the NG information region 56 having a predetermined size, the determining unit 26c causes display of the displayable number of IDs and " . . . " indicating that there are more IDs to be displayed, for example.

Furthermore, as illustrated in FIG. 10, when receiving an operation of placing the pointer 55 on the NG information region 56, the determining unit 26c causes display of an NG list 57 listing information related to an imaging protocol with which imaging has been determined as impossible, for example, similarly to the first embodiment described above. It should be noted that even when any other slice is selected, the determining unit 26c similarly makes an imaging possibility determination, causes display of the ID of an imaging protocol with which imaging has been determined as impossible in the NG information region 56, and causes display of the NG list 57 listing information related to the imaging protocol.

Figure 11:
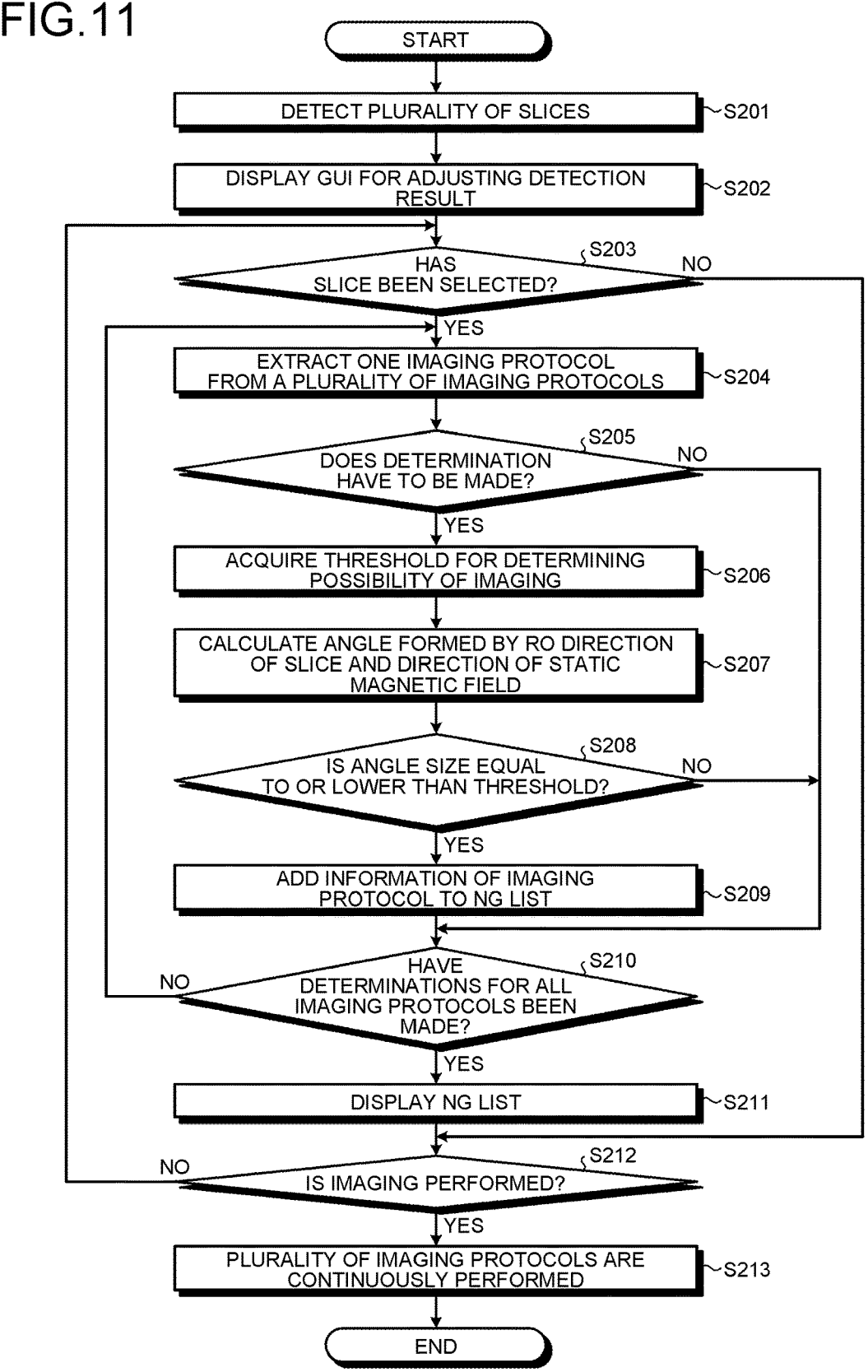
FIG. 11 is a flowchart illustrating a flow of imaging processing performed by an MRI apparatus according to the second embodiment.

FIG. 11 is a flowchart illustrating a flow of imaging processing performed by the MRI apparatus 100 according to the second embodiment. As illustrated in FIG. 11, in the MRI apparatus 100 according to the present embodiment, the detecting unit 26a firstly detects a plurality of slices of the subject based on an image of the subject (Step S201).

The planning unit 26b subsequently causes the display unit 25 to display a GUI for adjusting the detection result in accordance with a request from the operator (Step S202). The planning unit 26b also receives an operation of selecting a slice from the operator via the GUI for adjusting the detection result (Step S203). When the operation of selecting the slice is received by the planning unit 26b (Yes at Step S203), the determining unit 26c determines whether the imaging of the slice is possible with respect to a particular imaging protocol in the imaging protocols with which the slice is imaged.

More specifically, the determining unit 26c firstly extracts one imaging protocol from the imaging protocols (Step S204). The determining unit 26c then determines whether an imaging possibility determination has to be made with respect to the extracted imaging protocol (Step S205). In this process, when an imaging possibility determination has to be made (Yes at Step S205), the determining unit 26c acquires a threshold for making an imaging possibility determination of the imaging protocol from the imaging condition storage unit 23c (Step S206).

The determining unit 26c subsequently calculates the angle formed by the RO direction and the direction of the static magnetic field (Step S207) and determines whether the measure of the calculated angle is equal to or less than the threshold (Step S208). Thereafter, when the measure of the angle is equal to or less than the threshold (Yes at Step S208), the determining unit 26c adds information of the imaging protocol to the NG list (Step S209).

Thereafter, the determining unit 26c determines whether imaging possibility determinations have been made with respect to all the grouped imaging protocols (Step S210). It should be noted that when an imaging possibility determination does not have to be made (No at Step S205) or when the measure of the angle is equal to or less than the threshold (No at Step S208), the determining unit 26c does not add information of the imaging protocol to the NG list and determines whether imaging possibility determinations have been made with respect to all the grouped imaging protocols (Step S210).

Until the determining unit 26c makes imaging possibility determinations with respect to all the grouped imaging protocols (No at Step S210), the determining unit 26c repeats the processing from Step S204 to Step S209 as described above. Furthermore, when the determining unit 26c has made imaging possibility determinations with respect to all the imaging protocols (Yes at Step S210), the determining unit 26c causes display of the IDs of the imaging protocols included in the NG list in the NG information region and further causes the display unit 25 to display the NG list (Step S211). It should be noted that until the operation of selecting the slice is received by the planning unit 26b (No at Step S203), the determining unit 26c does not perform the processing from Step S204 to Step S211 described above and waits.

Thereafter, until an instruction to perform imaging is received by the imaging control unit 26d (No at Step S212), the planning unit 26b receives the operation of selecting the slice from the operator via the GUI for imaging planning (Step S203). Furthermore, when the slice has been selected by the operator (Yes at Step S203), the determining unit 26c makes an imaging possibility determination with respect to the grouped imaging protocols (Step S204 to Step S211). Furthermore, when an instruction to perform imaging is received by the imaging control unit 26d (Yes at Step S212), the imaging control unit 26d continuously performs the imaging protocols (Step S213).

As described above, in the MRI apparatus 100 according to the present embodiment, each time a slice is selected by the operator via the GUI for adjusting the detection result, an imaging possibility determination is made for each imaging protocol and information related to an imaging protocol with which imaging has been determined as impossible is displayed. With this configuration, when there is an imaging protocol with which imaging is stopped, the operator can be prompted to correct the imaging protocol.

When the planning unit 26b has received an operation of changing a plurality of imaging protocols with which the same slice is imaged from the operator, the determining unit 26c performs the processing at Step S202 to Step S206 described above, thereby acquiring a threshold for determining whether imaging is possible with respect to an imaging protocol requiring an imaging possibility determination out of the changed imaging protocols. With this configuration, even when a plurality of imaging protocols imaging the same slice have been changed, an imaging possibility determination of each imaging protocol after the change can be made.

As described above, in the MRI apparatus 100 according to the second embodiment, even when a plurality of slices are detected based on an image of the subject, an imaging possibility determination is made for each slice with respect to an imaging protocol with which there is a possibility that the imaging is stopped, before imaging is performed using each of the imaging protocols. With this configuration, when the same slice of the subject is imaged using a plurality of imaging protocols, the imaging using the imaging protocols can be prevented from being stopped in the middle of the imaging, similarly to the first embodiment. As a result, the same slice of the subject can be easily imaged using a plurality of imaging protocols, for example, whereby improvement of the diagnosis quality is expected, similarly to the first embodiment.

In the embodiments described above, examples have been described in which the measure of the angle formed by the RO direction of the slice and the direction of the static magnetic field is used as the index value. However, the index value is not limited thereto. For example, the determining unit 26c may calculate a predicted value of dB/dt as the index value. In this case, the determining unit 26c calculates a predicted value of dB/dt for each imaging protocol with reference to the imaging conditions stored in the imaging condition storage unit 23c.

Furthermore, in each of the embodiments described above, an example has been described in which a slice detected by the detecting unit 26a is imaged using a plurality of imaging protocols. However, the embodiments are not limited thereto. For example, even when a slice specified by the operator is imaged using a plurality of imaging protocols, similar embodiments can be performed. In this case, the planning unit 26b receives an operation of setting a slice on an image of the subject via a GUI for imaging planning from the operator, for example. Furthermore, when the slice is specified by the operator, before imaging is performed using a plurality of imaging protocols that have been grouped, with respect to at least one imaging protocol, the determining unit 26c determines whether the imaging of the slice specified by the operator is possible.

Furthermore, in each of the embodiments described above, an example has been described in which a slice is imaged as an imaging region. However, the embodiments are not limited thereto. The imaging region may be a slab (also referred to as a slice group) in which a plurality of slices are arranged in the direction of the thickness of each slice. Data collection for the slice described here is performed using a 2D sequence. Furthermore, the imaging region may be a three-dimensional region (volume region) specified when data collection is performed using a 3D sequence.

The 2D sequence described here is a pulse sequence collecting a two-dimensional slice image by performing encoding in the phase-encode direction and in the read-out direction with respect to one or more positions along the slice direction. Furthermore, the 3D sequence is a pulse sequence collecting three-dimensional volume data by performing encoding in the slice direction as well as in the phase-encode direction and in the read-out direction.

Furthermore, in each of the embodiments described above, an example has been described in which each time an operation of selecting or changing slice is received, a determination is made on whether the imaging of the slice is possible and the determination result is displayed in the NG list. However, the embodiments are not limited thereto.

For example, the determining unit 26c may automatically change the imaging conditions of each imaging protocol based on the determination result so that a series of imaging protocols can be continuously performed without a stop, instead of causing display of the NG list. In this case, after the imaging possibility determination of each imaging protocol is made, the determining unit 26c changes the imaging conditions of an imaging protocol with which imaging has been determined as impossible so as to eliminate the difference between an index value and a threshold, for example.

In this process, the determining unit 26c may cause the display unit 25 to display information indicating a parameter value of each imaging parameter included in the imaging conditions after the change.

Alternatively, with respect to an imaging protocol with which imaging has been determined as impossible, the determining unit 26c may cause the display unit 25 to display a parameter value representing an imaging condition with which the difference between an index value and a threshold can be eliminated as a candidate imaging condition, for example. In this case, the determining unit 26c receives a permission operation of permitting the candidate imaging condition with respect to each imaging protocol from the operator. Upon receiving the permission operation, the determining unit 26c changes the imaging conditions of each imaging protocol in accordance with the displayed candidate imaging condition.

Furthermore, the functions of the controller explained in each of the embodiments described above can also be achieved by software. For example, the function of the controller can be achieved by causing a computer to execute an imaging planning program specifying the procedures of the processing that has been described as performed by each controller. In this case, the imaging planning program is stored in a medium such as a hard disk or a semiconductor memory element and read out by a processor such as a CPU or a micro processing unit (MPU) to be executed, for example. Furthermore, the imaging planning program may be stored in a computer-readable recording medium such as a compact disc-read only memory (CD-ROM), a magnetic optical disk (MO), or a digital versatile disc (DVD) to be distributed.

According to at least one of the embodiments described above, when the same slice of the subject is imaged using a plurality of imaging protocols, the imaging using the imaging protocols can be prevented from being stopped in the middle of the imaging.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A magnetic resonance imaging (MRI) apparatus comprising:
   MRI processor circuitry configured to
   collectively receive, in a lump, on an image of a subject, an instruction for collectively setting a plurality of imaging protocols to be used for respectively corresponding MRI examinations of an imaging region; and
   determine propriety of the setting with respect to each of the plurality of imaging protocols before imaging is started using the plurality of imaging protocols,
   wherein the MRI processor circuitry determines the propriety of the setting based on an angle formed by a read-out direction of the imaging region and a direction of a static magnetic field.

2. The magnetic resonance imaging apparatus according to claim 1, wherein the MRI processor circuitry determines the propriety of the setting based on a predicted time rate of change in strength of a gradient magnetic field.

3. The magnetic resonance imaging apparatus according to claim 1, wherein the MRI processor circuitry determines the propriety of the setting based on the type of an imaging sequence or on an imaging condition used in the imaging protocol.

4. The magnetic resonance imaging apparatus according to claim 1, wherein the MRI processor circuitry
   receives an operation of selecting or changing the imaging region from an operator, and
   determines the propriety of the setting each time the operation is received.

5. The magnetic resonance imaging apparatus according to claim 1, wherein the MRI processor circuitry determines the propriety of the setting with respect a particular imaging protocol of the imaging protocols.

6. The magnetic resonance imaging apparatus according to claim 1, wherein the MRI processor circuitry determines the propriety of the setting with respect to an imaging protocol using an echo planar imaging (EPI) sequence.

7. The magnetic resonance imaging apparatus according to claim 1, wherein the MRI processor circuitry causes a display unit to display information for identifying an imaging protocol determined as unsuitable for the setting.

8. The magnetic resonance imaging apparatus according to claim 1, wherein the MRI processor circuitry calculates an index value related to influences of imaging on the subject or image quality and compares the index value and a predetermined threshold so as to determine the propriety of the setting.

9. The magnetic resonance imaging apparatus according to claim 8, wherein the MRI processor circuitry causes a display unit to display information indicating a difference between the index value and the threshold with respect to an imaging protocol determined as unsuitable for the setting.

10. The magnetic resonance imaging apparatus according to claim 1, wherein the MRI processor circuitry causes a display unit to display information serving as a guide to set an imaging region suitable for an image protocol determined as unsuitable for the setting.

11. The magnetic resonance imaging apparatus according to claim 1, wherein the MRI processor circuitry is further configured to:
   detect an imaging region of the subject based on the image of the subject, and
   when the detected imaging region is imaged using a series of imaging protocols, the MRI processor circuitry receives instruction to set a plurality of settings for the imaging region with each imaging protocol in one lump.

12. The magnetic resonance imaging apparatus according to claim 11, wherein the MRI processor circuitry has been configured to
   detect a plurality of imaging regions of the subject, wherein
   when imaging each of the imaging regions using the series of imaging protocols, with respect to each of the imaging regions, the settings of the imaging region with each imaging protocol are received in a lump, and
   with respect to each imaging protocol, the propriety of the setting for each of the imaging regions is determined.

13. A magnetic resonance imaging (MRI) planning method comprising:
   collectively receiving, in a lump, on an image of a subject, an instruction to set a plurality of settings of an imaging region, wherein the settings of the imaging region are set for a plurality of respective imaging protocols included in at least part of a series of imaging protocols to be performed in an examination a subject, and determining propriety of the setting for each imaging protocol included in the part of the imaging protocols before imaging is started using the part of the imaging protocols, wherein the propriety of the setting is determined based on an angle formed by a read-out direction of the imaging region and a direction of a static magnetic field.

* * * * *